United States Patent [19]
Kaish et al.

[11] Patent Number: 6,025,200
[45] Date of Patent: Feb. 15, 2000

[54] METHOD FOR REMOTE DETECTION OF VOLATILE TAGGANT

[75] Inventors: Norman Kaish, Whitestone; Jay Fraser, Merrick; Volkan Otugen, Brooklyn, all of N.Y.; Svetozar Popovic, Norfolk, Va.

[73] Assignee: Tracer Detection Technology Corp., Syosset, N.Y.

[21] Appl. No.: 08/771,608

[22] Filed: Dec. 21, 1996

[51] Int. Cl.[7] .................................................. G01N 33/22
[52] U.S. Cl. ........................ 436/56; 436/164; 436/816; 436/27; 422/83; 73/23.2
[58] Field of Search .............................. 436/56, 164, 805, 436/902, 27, 816; 422/83, 90; 73/23.2, 23.36

[56] References Cited

U.S. PATENT DOCUMENTS

| | | |
|---|---|---|
| 3,991,680 | 11/1976 | Dietz et al. . |
| 4,256,038 | 3/1981 | Dietz et al. . |
| 4,944,921 | 7/1990 | Colby et al. ............................. 436/175 |
| 5,345,809 | 9/1994 | Corrigan et al. ......................... 73/23.2 |
| 5,409,839 | 4/1995 | Balestrieri et al. . |
| 5,585,575 | 12/1996 | Corrigan et al. ..................... 73/863.71 |

*Primary Examiner*—Lyle A. Alexander
*Attorney, Agent, or Firm*—Milde, Hoffberg & Macklin, LLP

[57] ABSTRACT

A method of tagging and detecting objects is disclosed which comprises the steps of: (a) applying a volatile taggant to the object; and (b) subsequently detecting the presence of the taggant by the absorption, transmittance, reflectance, photon emission or fluorescence of the taggant and therefore a proximity of the tagged object. The present invention therefore provides optical sensing means which do not require physical separation of differing compounds for discrimination thereof.

41 Claims, 5 Drawing Sheets

METHOD FOR REMOTE DETECTION OF VOLATILE TAGGANT

FIELD OF THE INVENTION

The present invention relates to the filed of chemical tracer detection, and more particularly to infrared, visible and ultraviolet absorption, reflection, transmittance, emission or fluorescence characterization of chemical tracers.

BACKGROUND OF THE INVENTION

Tracers are volatile compounds added to various substances for the purpose of tagging and tracking the course of that substance in the environment. Known tracer vapors are be detectable at very low levels—parts per trillion (pp $10^{12}$) or less. Such tracers, when used appropriately, generally have no impact on health or the environment and are economically practical in the tagging of substances such as air, gas, liquids, and even solids.

U.S. Pat. Nos. 3,991,680 and 4,256,038 relate to methods of detecting small bombs to provide security against terrorist activities which can cause the destruction of civil aircraft in flight or detonate explosives in places where large groups of people congregate. These methods involve the tagging of explosive materials such as blasting caps with a so-called "vapor taggant" which can be "sniffed" and detected by suitable equipment. The vapor taggant disclosed in U.S. Pat. No. 3,991,680 is sulfur hexafluoride ($SF_6$) absorbed in a fluoro-polymer. The vapor taggant disclosed in U.S. Pat. No. 4,256,038 is a Perfluorocarbon Tracer ("PFT") which includes one or a plurality of the following compositions: perfluorocycloalkanes such as perfluorodimethylcyclobutane (PDCB), perfuoromethylcyclohexane (PMCH), and perfluorodimethylcyclohexane (PDCH); perfluoroaromatics such as hexafluorobenzene (HFB), octafluorotoluene (OFT), decafluorobiphenyl (DFBP), decafluoroxylene (DFX), octafluoronaphthalene (OFN), and pentafluoropyridene (PFP), perfluoroalkanes such as perfluorohexane (PFH), perfluoropentane (PFPT), and perfluorooctane (PFO), and perefluorocycloalkenes such as decafluorocyclohexene (DFCH) and octafluorocyclopentene (OFCP).

The disclosure of U.S. Pat. No. 4,256,038 is expressly incorporated herein by reference.

As disclosed in these patents, the detection system for explosives consists of:

(1) "taggants" (for example, the Perfluorocarbon Tracers, or "PFTs") that give off detectable inert tracers when applied to materials; and (2) a sensing system capable of detecting taggants in the atmosphere.

Taggant use involves the detection of inert gaseous vapors in minor tracer quantities that are emitted over time. As there are a plurality of separate tracers in the PFT family, each with its own "fingerprint", the PFTs can be combined in a range of combinations and concentrations, yielding thousands of discrete "signatures". This allows discrimination between various taggants and enables the individual detection of multiple products, or the tracking of individually tagged products to provide exact identification and location.

The Perfluorocarbon Tracer technology is believed to be the most sensitive of all known tracer technologies because the ambient background levels of the routinely used PFTs are extremely low, for example in the range of parts per quadrillion—ppq range. Therefore, because of this low "noise", the sensitivity of detection is dependent on the sensing instrument technology. Many of the PFT compounds, which are invisible and environmentally and biologically safe to use, are presently commercially available.

Various methods of detection have been demonstrated conclusively in numerous application projects for PFTs including indoor heating and ventilation studies, underground leak detection and long range atmospheric studies.

The following provides a simplified description of how the PFT tracers have heretofore been detected and analyzed, in order to understand some advantages of PFTs over other gaseous and non-gaseous tracers. The PFTS can be analyzed by gas chromatography wherein the constituents of an air sample are thermally absorbed from a sample tube and are injected into the carrier gas stream via a sample valve (in a building structure, multiple sampling tubes are run throughout the different regions of the building being monitored). Before entering the chromatography column, all the components are present as a "slug". After passing through the column, the constituents are physically and temporally separated to an extent that depends on the nature and conditions of the column.

The high affinity of PFTs for reaction with electrons also makes them some of the most sensitive compounds for detection in an Electronic Capture Detector (ECD), which is a small (0.1 to 0.2) ml. reaction chamber containing an electron source. The cloud of electrons in the chamber is periodically collected, producing a current. When tracer molecules enter the cell, the reacted electrons cannot be collected. The resulting reduction in current is a measure of the PFT concentration.

However, the atmosphere contains many components, the concentrations of which exceed those of the PFTs, and that are detectable in the ECD used to measure the PFTs. Included are $O_2$, nitrogen oxides, chlorofluorocarbons (CFCs), $SF_6$, and others, each of which could interfere with the early eluting PFTs. Physical means are used (e.g., sampling onto an absorbent with subsequent purging) to remove most of the oxygen and some of the CFCs. A catalyst bed operating at about 200° C. is needed to destroy many remaining interfering compounds so that the surviving PFTs can be detected.

Sample collection is accomplished by several means. Inexpensive passive Capillary Absorption (sampling) Tubes (CATS) allow the monitoring of surveillance areas in remote or congested locations. These sampling tubes are collected and sent to a laboratory for analysis. Alternatively, a real time Continuously Operating Perfluorocarbon Sniffer (COPS) can provide immediate indications of the source of PFT emissions. Both the COPS and the ECD are commercially available.

It is the physical and chemical inertness of the PFTs that not only prevents their loss in the atmosphere, but also helps in their separation and analysis from less stable interfering compounds and makes them biologically inactive; and thus safe to use. Their limited industrial use not only results in low ambient background concentration, but also precludes the possibility of numerous higher local concentrations that might confuse detection capability.

PFT technology has already been developed and utilized in various applications including: (1) detection of leaks in underground storage tanks; (2) detection of leaks in high-pressure, oil-filled electric transmission lines; (3) atmospheric tracing and air pollution dispersion studies; (4) building ventilation studies and (5) detection of tagged explosives blasting caps in airline luggage. Investigation is underway for exploring the application of PFTs to the detection of leaks in natural gas pipelines and to early warning fire detection systems.

Effective inspection of large containers and trucks for controlled substances and narcotics is essential for the success of drug interdiction efforts. A significant fraction of drugs are smuggled through this avenue. Without prior knowledge provided through intelligence activities, the chances for drug detection are very slim. A successful drug interdiction program therefore requires efficient, rapid and cost-effective inspection techniques for large objects. The technique heretofore used to thoroughly inspect containers is manual, highly labor intensive and can hardly be expanded to meet the challenge of abating the flow of illicit drugs from one country to another. Hence, the only way to achieve the goal of an effective counter-drug effort is to develop a rapid, automatic, non-intrusive inspection system to inspect shipments and cargo containers without removing all of the contents for manual inspection, U.S. Pat. No. 5,409,839, expressly incorporated herein by reference, is entitled and describes "A Method for the Tagging and Detection of Drugs, Crops, Chemical Compounds and Currency with Perfluorocarbon Tracers." The methods of detection mentioned in that patent are gas chromatography and electron capture detection. The limitations of these methods of detection are set forth herein.

SUMMARY OF THE INVENTION

The present invention relates to the use of optical (infrared, visible and ultraviolet) detection techniques to fully exploit the potential of chemical tagging technology (i.e., emitting/evaporating tags and microencapsulated tags) especially as a tactical tool in the surveillance of contraband movement, in the detection and recognition of sensitive documents, including currency, and in a range of other law enforcement applications. The present invention relates to the use of optical techniques to detect the absorption, transmittance, reflectance or fluorescence of chemical taggants.

A preferred chemical taggant genus includes perfluorocarbon compounds, which have unique spectral signatures, low ambient concentrations, and may be provided in suitable forms having extended release profiles. Further, these may be detected at extremely low concentrations and thus may generally be applied to tagged objects in a manner which prevents untagging, until the taggant is exhausted. The preferred taggants are also chemically stable, and thus may be admixed with explosive compositions or used in otherwise hostile environments without loss of tagging ability.

While the perfluorocarbons as a group tend to have these aforementioned properties, the present invention also encompasses the use of other taggants, as well. For example, it may be desirable to provide a derivative or modified perfluorocarbon or hydrofluorocarbon compound having enhanced or specific detection characteristics which makes it especially suitable for particular applications. Thus, it may be desirable to provide a remote detection system which, for example, is capable of detecting taggant at a distance of up to 1 km. In this case, the use of UV laser induced fluorescence as a detection scheme is very advantageous. This is because the emission source has an inherent low spreading over long distances and narrow band spectral characteristics, as well as a relatively high intensity at the particular emission wavelength, the fluorescence pattern is not masked by the emitted light, and such systems do not generally require any change in the emitted light wavelength during use. Thus, derivatization of perfluorocarbon compounds, such as by inclusion of linear or cyclic ethers or thioethers; pyridine, pyrimidine and triazine structures; alkene structures or extended aromatic bridging; bromine or chlorine substitution for fluorine; heteroclylic structures; nitrogen, oxygen or oxygen moieties, or other types of compounds. For example, it is believed that the heterocyclic compound pentafluoropyridene (PFP) has different UV-fluorescent properties over its analogue, hexafluorobenzene, which may be advantageous in detection and discrimination for use as a taggant. It is noted that some of these perfluorocarbon-derivative compounds may be toxic or have detrimental environmental effects; however, since they are used in very low amounts and release over an extended period, these may still be acceptable for use under certain circumstances. Fluorescent Brighteners are known, and the chemical principles for creation of such compounds may also be applied to provide volatile, environmentally stable, generally invisible taggant compositions. See, Kirk Othmer Encyclopedia of Chemical Technology, Vol. 4, p. 213–226, incorporated herein by reference.

More specifically, the vapor taggant technology, including PFTs can be used for the tagging and detection of illicit drugs, crops, chemical compounds, currency and other illicit drug-related materials. These taggants may also be used to track persons, vehicles, goods in commerce, and paths. In some instances, such as the determination of authenticity, the absence of taggant may be used to indicate counterfeiting. In this case, the taggant is preferably released upon inspection of goods, and normally the goods do not release taggant, allowing the taggant to remain for long periods, such as months or years, while increasing the efficiency of use.

Unlike chemical detection, which relies on air sampling to establish the presence of emitting/evaporating tags, spectral characteristic detection systems can detect the presence of encapsulated tags or spatially separated regions of taggant, in the manner of bar codes (as well as emitting/evaporating tags) by the detection of absorption, transmittance, reflectance or fluorescence which may not require air sampling and thus makes possible a further range of applications of the tracer technology, in particular the use of non-volatile or low-volatility taggants, remote sensing, and spatially separated taggant zones on the same object. Therefore, spectral characterization techniques can may be employed in detection instruments which are (i) capable of real-time measurements, (ii) simple to operate, (iii) capable of detecting taggants at low concentrations, e.g., perfluorocarbon tracers (PFTS) at or below the level of one part per billion, (iv) and capable of detecting encapsulated taggants. The spectral characteristic sensors according to the present invention can thus instantly detect extremely low levels of taggant and may be suitable for remote surveillance and monitoring. Additionally, the spectral characteristic detection methods may be employed in hand-held detection devices, as well as fixed location devices (capable of detecting tagged documents or currency passing through copying or counting equipment, for example). Spectral characteristic detection of the taggants makes possible the use of national overhead assets, e.g., satellites, aircraft, etc., to detect tagged materials, even through cloud cover, depending on the particular wavelength measured.

By employing laser illumination, the advantages of coherent detection may be employed. In this case, the return signal corresponds to a delayed emitted signal. Thus, if the temporal coherence of the laser is sufficient, or a high fidelity delayed laser signal is available, the received signal may be detected with high sensitivity. In this case, in order to obtain a number of spectral sample points, the laser must be tunable or a plurality of sensing systems employed. In a coherent detection system, the effect of ambient illumination may be greatly reduced, and there is no need for separate tuning of the illumination system and detection systems responsivity.

It is a principal object of the present invention to provide a method of surveillance of contraband movement, for the spectral characteristic detection and recognition of sensitive documents, including currency, and in a range of other law enforcement applications.

It is also an object of the present invention to optically detect illicit drugs, crops, chemical compounds and currency with taggants, preferably Perfluorocarbon Tracers (PFTs), for the identification and tracking of illicit drug-related materials, production facilities and activities.

It is a further object of the present invention to provide a spectral characteristic detection system that, unlike chemical detection, does not rely on air sampling to establish the presence of emitting/evaporating tags.

It is an object of the present invention to provide a optical detection system that, unlike chemical detection, can detect the presence of encapsulated tags or spatially separated zones, i.e., "bar codes" (as well as emitting/evaporating tags) by the use of an optical scanning system which provides illumination to the suspected taggant and detection of the spectral characteristics, e.g., absorption, transmittance, fluorescence, reflection or emission which does not require air sampling and thus makes possible a further range of applications of the tracer technology. The illumination source may be, for example a laser with IR, visible or UV emission, a maser, LED, flash lamp, incandescent light source, fluorescent light source, electrical discharge or gas-discharge light source, or even sunlight.

It is another object of the present invention to provide a technique that can be implemented to develop spectral characteristic detection instruments which are capable of real-time measurements.

Yet another object of this invention is to provide a taggant detection technique that is simple to operate.

It is a still further object of this invention to provide a spectral characteristic detection technique that is capable of detecting perfluorocarbon tracers (PFTs) at or below the level of one part per billion.

It is another object of the present invention to provide a laser technique that is capable of detecting encapsulated PFTs.

It is another object of the present invention to provide an optical sensor that can instantly detect extremely low levels of PFTs and would also be suitable for remote surveillance and monitoring.

It is another object of the present invention to provide a method that can be employed in hand-held detection devices, as well as fixed-location devices (capable of detecting tagged documents or currency passing through copying or counting equipment, for example).

It is further object of the present invention to provide a system that manufacturable to produce a reliable, sensitive, and usable system, capable of withstanding high levels of scrutiny, such as under the American judicial system.

It is a still further object of this invention to provide a means for the use of national overhead assets, e.g., satellites, aircraft, etc., to detect tagged materials, even through cloud cover.

These objects, as well as further objects which will become apparent from the discussion that follows, are achieved, in accordance with the present invention, by a method comprising the steps of
(a) applying a taggant to the contraband or sensitive documents; and (b) subsequently using a light to detect the presence of said taggant by the spectral characteristics of absorption, transmittance, reflectance, emission or fluorescence of the taggant and therefore the contraband or sensitive documents.

PREFERRED EMBODIMENTS OF THE INVENTION

Figure 1:
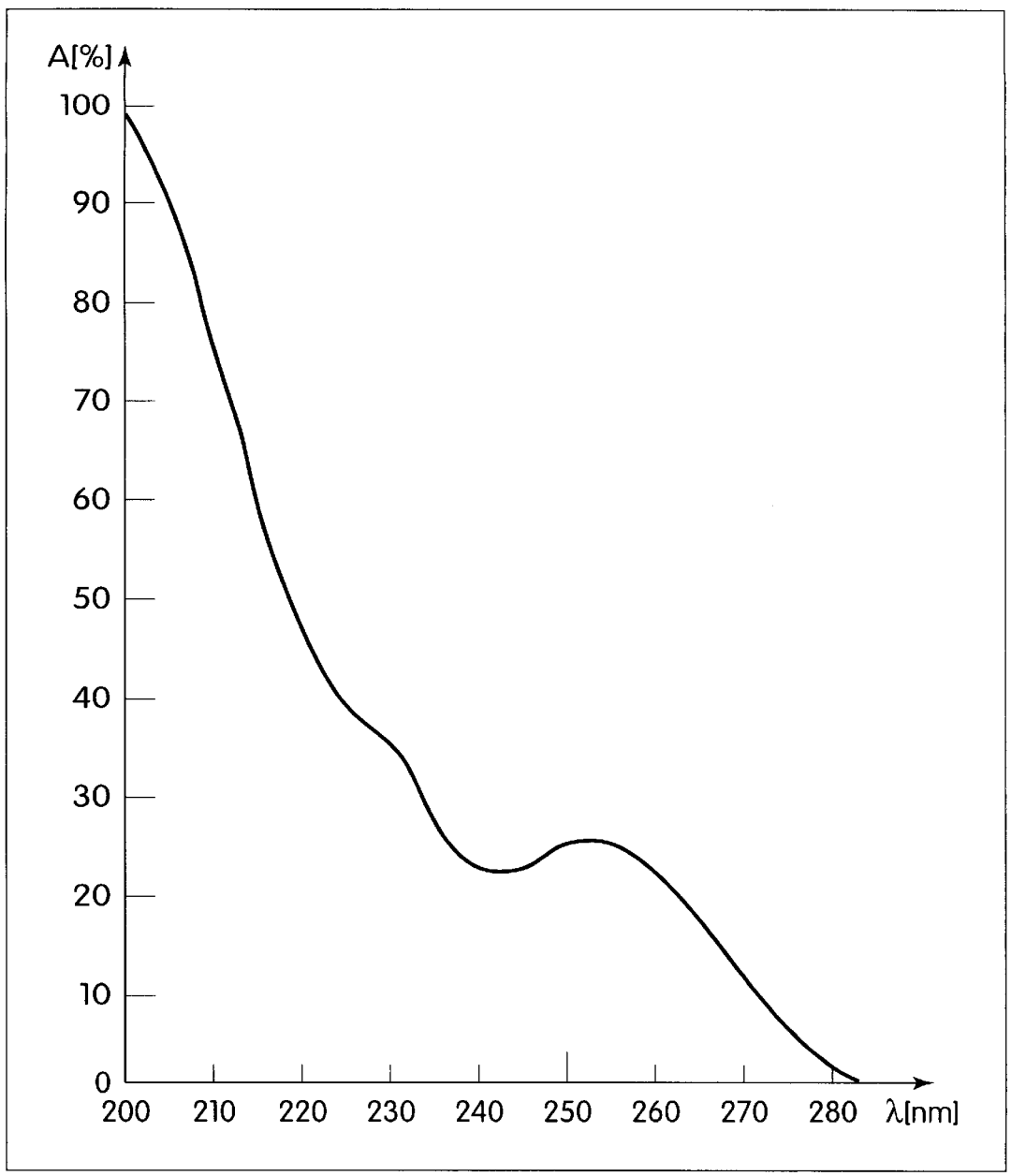
FIG. 1 is a spectrophotometric scan of perfluorodimethylcyclohexane in the ultraviolet section of the spectrum.

The optical detection system of the invention can be operated locally, remotely or by sampling means. The first two means are preferred because they are non-intrusive. The light used to illuminate the PFT taggant is in the ultraviolet, visible or infrared sections of the electromagnetic spectrum, or in a combination of two or all of those sections.

The currently preferred applications for the invention are:
A. Optical Detection & Recognition of Sensitive Documents,
B. Laser-Induced Fluorescence-Based Detection of PFT, PFT-derivative or PFT analogue Emissions,
C. Remote Optical Surveillance of Urban Structures, and
D. Tracer Technology Using National Overhead Assets.

These applications are discussed below.

A. Optical Detection & Recognition of Sensitive Documents

A compact, laser-based system may be provided to detect and recognize PFT tagged documents. In this case, the system provides means for the prevention of unauthorized handling of pretagged or coded documents and the detection and verification of currency. Documents are of interest because the field of making markings on documents is well developed. Further, the application of microencapsulated compounds in printing inks is also well developed, e.g., "scratch and sniff" markings and perfume samples. Therefore, the present invention includes the application of existing composition application techniques for the tagging of documents.

In this case, it should be understood that odoriferous compositions may also be considered taggants, and may be detected by their respective unique spectral characteristics. However, these compositions, in general, are not preferable for many applications because of their odor, ease of determination of presence by persons or animals without specialized detection equipment, and limited lifetimes as continuous volatile emission taggants.

Recent advances in solid-state laser and electro-optic technologies make possible non-destructive, real-time, laser-based detectors, capable of optically sensing tagging compounds. Therefore, such sensors may, according to the present invention be provided in paper-handling apparatus, such as copiers, currency verification machines, and the like. By providing a remote sensing scheme, rather than chemical detection, high speed optical sensing systems may be employed, allowing high throughput. Typical chemical taggant detection systems have response times measured in seconds or longer, while optical systems may operate in millisecond timescale. In such detectors, a signal, which may include infrared, visible or ultraviolet rays, is received. Generally, a plurality of detectors are provided which each respond to a different wavelength, although a single detector may scan various wavelengths. The wavelength pattern of the received signal is then compared with known patterns, and the presence or absence of the taggant determined based on a unique set of spectral characteristics. This technology has practical application in the areas of detecting tagged currency and sensitive documents.

Laser methods are of particular interest because of their high specific power at a given wavelength and low spatial dispersion over distance. In addition, for certain types of measurements, the phase and time coherence patterns may be useful in corresponding detector design. Thus, lasers may be used to efficiently illuminate a remote object or portion of an object with a desired wavelength illumination, with a resulting spectral pattern or modification measured remotely. For example, laser-induced fluorescence exploits a specific property of the substituted hydrocarbon family (of which PFTs are members): such compounds tend to absorb light in the ultraviolet (UV) range between 190 to 280 nm and in return emit light in the form of fluorescence in the 250 to 350 nm range.

FIG. 1 is a spectrophotometric scan of perfluorodimethylcyclohexane in the ultraviolet section of the spectrum showing three absorption bands starting from 280 nm, with peaks or shoulders around 260, 220 and 200 nm.

Unauthorized handling of sensitive documents which have been pre-tagged or coded can be monitored and prevented, in a non-destructive manner, using spectral characteristic detection technology. For example, an optical system may be incorporated into photocopying and shredding machines within an office environment, to instantly detect and recognize the manipulation of sensitive (pre-tagged) documents, for example, attempts to make unauthorized copies or to destroy documents by shredding.

By employing preferred taggants according to the present invention, the permanent tagging of sensitive documents can be vapor-less and invisible to the naked eye. For example, PFTs may be encapsulated in polymer compositions and structures, including but not limited to liposomes, polysaccharides, polymers and plastics such as polyvinylidene fluoride (PVDF), and the like to ensure its durability. The detection system in this application is compact enough to be installed in conventional office machines. Typically, PFT concentrations in this application will be very large compared to those in the vapor-based applications which will be discussed below. Therefore, sufficiently high concentration levels will be obtained that are useful with compact solid-state lasers and photodetectors. Further, the light source in this application need not be a laser, and thus other available light sources with suitable wavelength or spectral output may be used, such as the illumination source of a copier.

Figure 2:
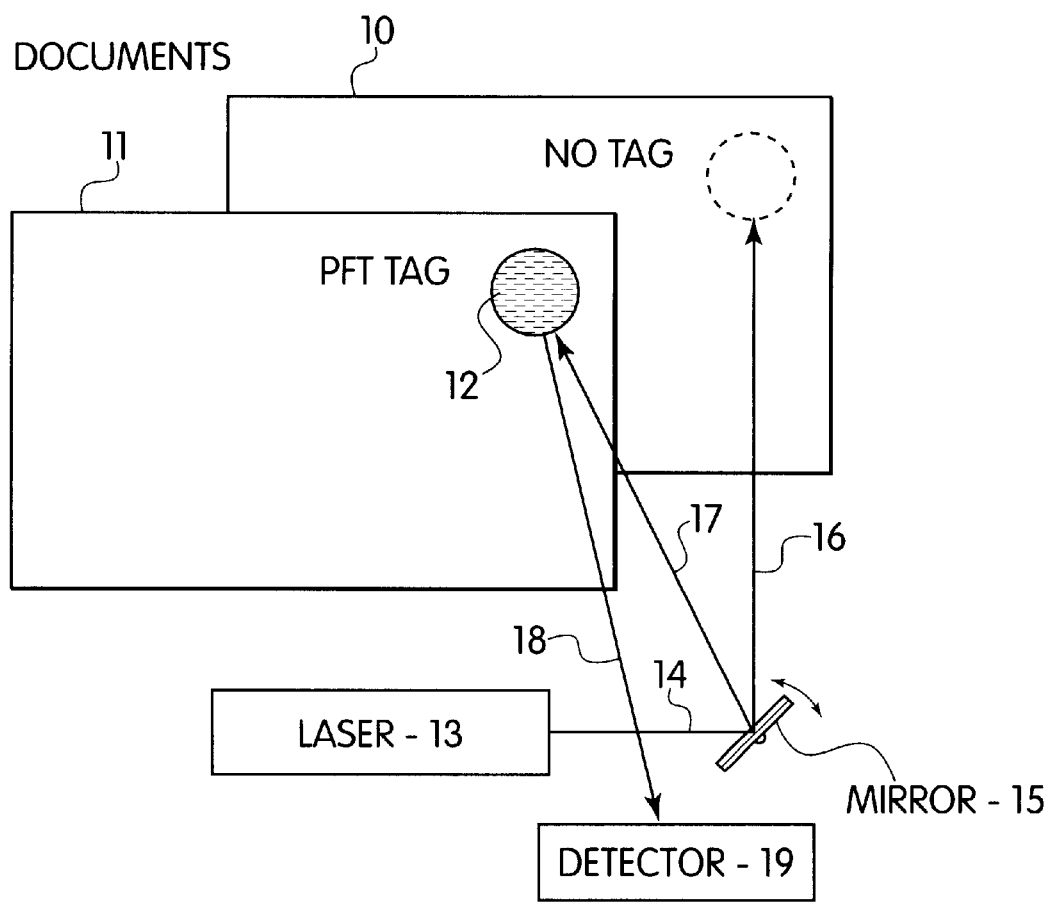
FIG. 2 shows two documents, one of which is marked with a non-evaporative PFT taggant; a laser beam in the ultraviolet section of the spectrum is directed by a movable mirror first to the untagged document and then to the PFT-tagged document where the absorption, reflectance or fluorescence induced by the laser beam is measured to the spectrophotometric detector.

FIG. 2 shows two documents, 10 and 11, one of which, 11, is marked with a non-evaporative PFT taggant 12. A laser 13 emits a laser beam in the ultraviolet section of the spectrum 14, which is directed by a movable mirror 15 first 16 to the untagged document 10 and then 17 to the PFT-tagged document 11 where the fluorescence induced by the laser beam is reflected 18 to the spectrophotometric detector 19.

B. Optical Detection of PFT Emissions

A high-sensitivity, wide-dynamic range PFT gas detection device may be provided for the detection of very low levels of these compounds in air. Detection of PFT emitted into the air by pre-tagged materials allows the surveillance of contraband movement.

While chemical analysis systems for PFT detection are currently available, they are inherently limited because they depend on air sampling and therefore require the employment of a mechanical air sampling device or "sniffer," which must be in the same physical environment as the taggant. Furthermore, these devices have limited dynamic range which makes continuous sampling across orders of magnitude change in PFT concentration, at best, difficult. The spectral characteristic detection systems, particularly laser-based optical systems, hold the promise of detecting PFT-emissions nonintrusively as they would not require the collection of air samples. In addition, the dynamic range of the spectral detectors can be changed instantaneously or quickly, allowing the continuous operation of the system from the time when the PFT is first detected up to the time of positive identification of the location of tagged material.

One such detection system will consist of a laser as a UV source (Nd:YAG-based or Excimer laser) and photodetection equipment capable of sensing extremely low levels of absorption, transmittance, reflectance or fluorescence.

While these systems capable of the required performance are typically not solid state devices, the present invention also includes the use of solid state lasers and detectors, allowing the system to be miniaturized and the operation simplified. For example, a handheld spectral characteristic-based PFT detection system may be provided, which would operate continuously and be able to instantaneously detect extremely low levels of PFT in air.

A spectral characteristic detector system requites that a unique or quasi-unique spectral characteristic pattern, or signature of a taggant to be detected and distinguished from other possibilities. Thus, the spectral characteristics of each of the employed taggants must be determined, as well as of common contaminants and trace materials, so that the system can distinguish, at low concentrations or in low amounts, the presence of taggant from the presence of innocuous or irrelevant compositions. This library of spectra may be compiled from known environmental data, as well as empirical data about the taggants of interest. The library therefore potentially allows discrimination of spectral patterns of potential interference from the signature of one or more taggants. It is noted that, as generally employed, and unlike chemical sensing systems, no physical separation is attempted between the taggant and the environment, so that the spectral signature of the taggant is superimposed on any background patterns. Therefore, by its very nature, the system must determine the spectral characteristics at a plurality of wavelengths in order to distinguish, with high reliability, the presence and amount of taggant. Further, in order to enhance the uniqueness of a tagging scheme, various taggants, such as a mixture of PFTs or PFT derivatives, may be provided simultaneously, so that the spectral characterization, in this case, must also distinguish between the various taggants.

While the characterization may be additive, i.e., looking for a unique pattern superimposed on a background pattern, advantages in detection may also be found by using a subtractive technique, i.e., identifying a various compositions within the field of view, by the same spectral characterization process or by differing means, and compensating for the effect of those compositions by subtracting their effect from the observed effect. By identifying the most significant interfering compositions, the problem of detecting the taggant may be simplified.

C. Remote Optical Surveillance of Urban Structures

A vehicle-borne remote taggant spectral characteristic detection system can be used for the purpose of surveillance and monitoring of urban structures for monitored objects, such as illegal drugs, banknotes, etc.

For example, a remote detection system may be provided capable of scanning a street from a distance, determining which buildings, if any, house tagged material. In order to implement this new technology, sensing techniques currently used in LIDAR technology, developed for atmospheric studies, may be employed, especially where the emission of the laser is set in the near-ultraviolet spectral range, or otherwise in the spectral range necessary to match the properties of tracer compounds and produce an identifiable signature. The system can thus perform instantaneous measurements and therefore will provide immediate information from a distance of up to a thousand feet and more. The system developed can be simple to operate and moveable (for example, vehicle borne).

Figure 3:
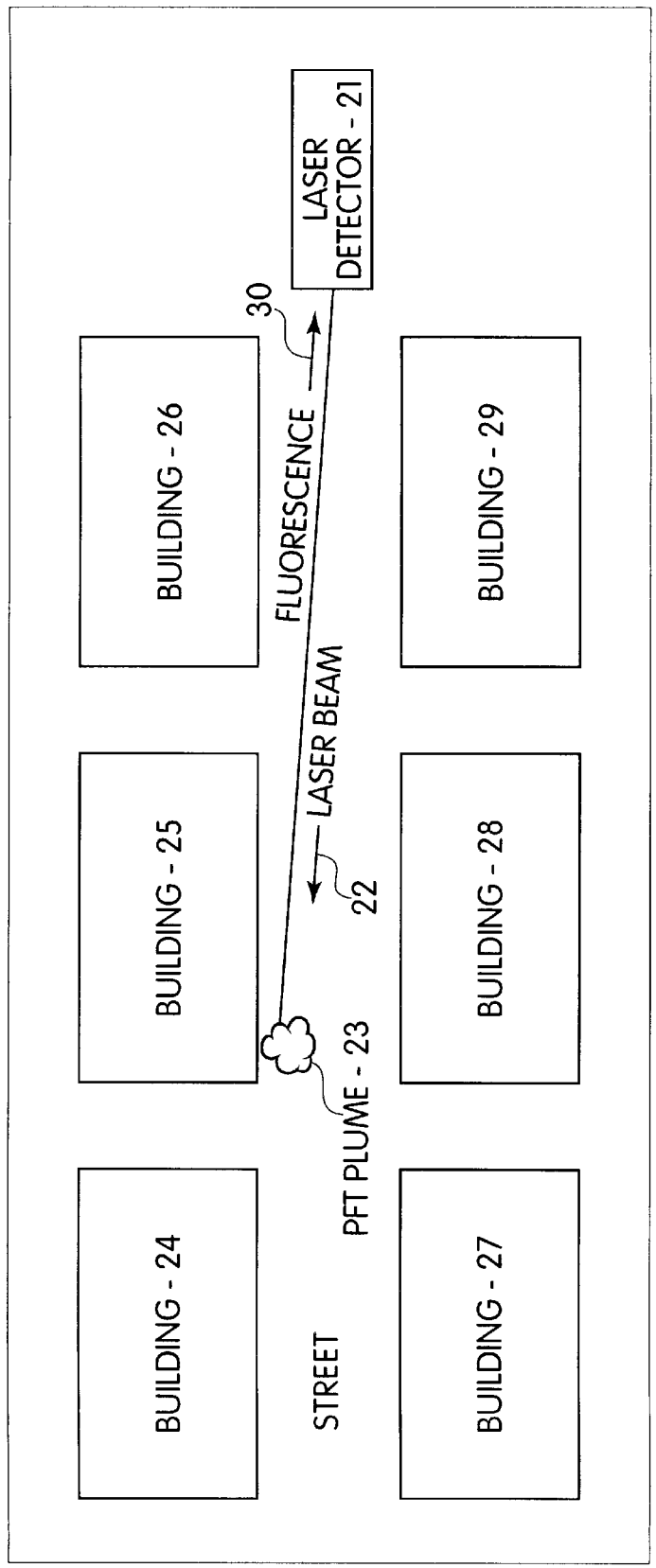
FIG. 3 is a diagram, showing a laser beam from a laser detector directed to a PFT plume emanating from an evaporative PFT from PFT-tagged contraband within a building; the absorption, reflectance or fluorescence of the PFT plume is detected by the laser detector.

FIG. 3 is a diagram showing a laser detector 21, emitting a laser beam 22 directed to a PFT plume 23 emanating from an evaporative PFT from PFT-tagged contraband within a building 25, one of a group of buildings 24–29 on either side of a street depicted in FIG. 3. The absorption, reflectance, emission or fluorescence 30 of the PFT plume 23 is detected by the laser detector 21. (If a detector or reflector may be located behind the PFT plume 23, then transmission characteristics may also be measured.) It is easy to direct the laser beam 22 from the laser detector 21 to any one of the buildings in turn, in order to detect the one emitting a PFT plume 23.

D. Tracer Technology Using National Overhead Assets

Locating tagged contraband using national overhead assets requires matching the stimulated spectral emissions of the taggants with the surveillance capability of existing and planned sensor systems. In this case, environmental illumination is generally used, or a land-based or aircraft-based illuminator system would be used to stimulate the taggant plume over the facility to be monitored. Preferably, the illuminator is a pulsed, high energy laser which could provide stimulation at the wavelength at which the taggant is most sensitive and which would produce an absorption, reflectance or fluorescence signature, to which the remote sensor is responsive. The wavelength must also be within at least one of the bands of atmospheric transmission in which a sensor can see to the ground (i.e., the MWIR band around 3.1 μm or the visible band above 0.4 μm).

The requisite sensor systems can be either in geostationary orbit or low earth orbit since the event to be monitored is cooperative. In other words, the illuminator can be triggered exactly when a sensor in low earth orbit is passing over the geographical region of interest. A sensor in geostationary orbit would have the region in its field of regard constantly. The illuminator could be triggered when the geostationary sensor's line of sight is pointing at the region of interest. In addition, if the illumination source has a unique signature, this may be detected and correlated with the detected pattern; Thus, the ambient conditions may be determined (when the illumination source is inactive) and this background subtracted from the received specific spectral pattern due to the illumination.

A pulsed laser for the illuminator is therefore desirable due to its high peak power capability as well as for the sensor's ability to discriminate between a pulsed emanating signal from stimulated contraband and the steady state earth background. A pulsed signal at a known frequency can thus provide a higher signal to noise ratio at the sensor than a steady state signal. Furthermore, since the illuminator is cooperative, the sensor can be synchronized to the illuminator and thus benefit from the higher sensitivity available from a synchronous detector.

Of course, where an illumination source is controlled, this may be integrated with a detection system, reducing the need for the use of national overhead assets.

Figure 4:
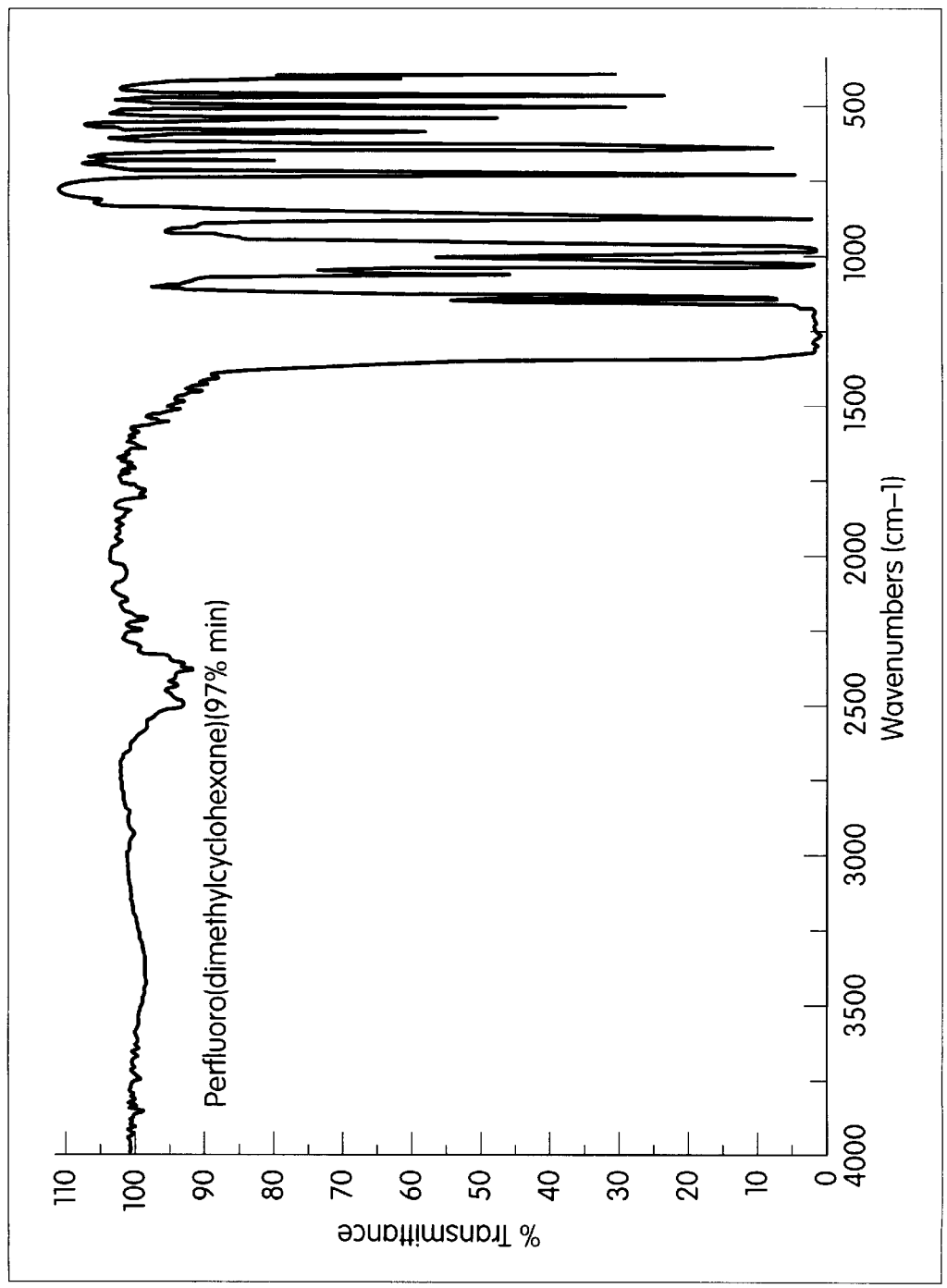
FIG. 4 is a spectrophotometric scan in the infrared section of the spectrum (4000 to approximately 500 Wavenumbers [$cm^{-1}$]) for perfluorodimethylcyclohexane.

FIG. 4 is a spectrophotometric scan in the infrared section of the spectrum (4000 to approximately 500 Wavenumbers [$cm^{-1}$]), showing the transmittance of perfluorodimethylcyclohexane. The specific details of the analysis are given in FIG. 4.

Figure 5:
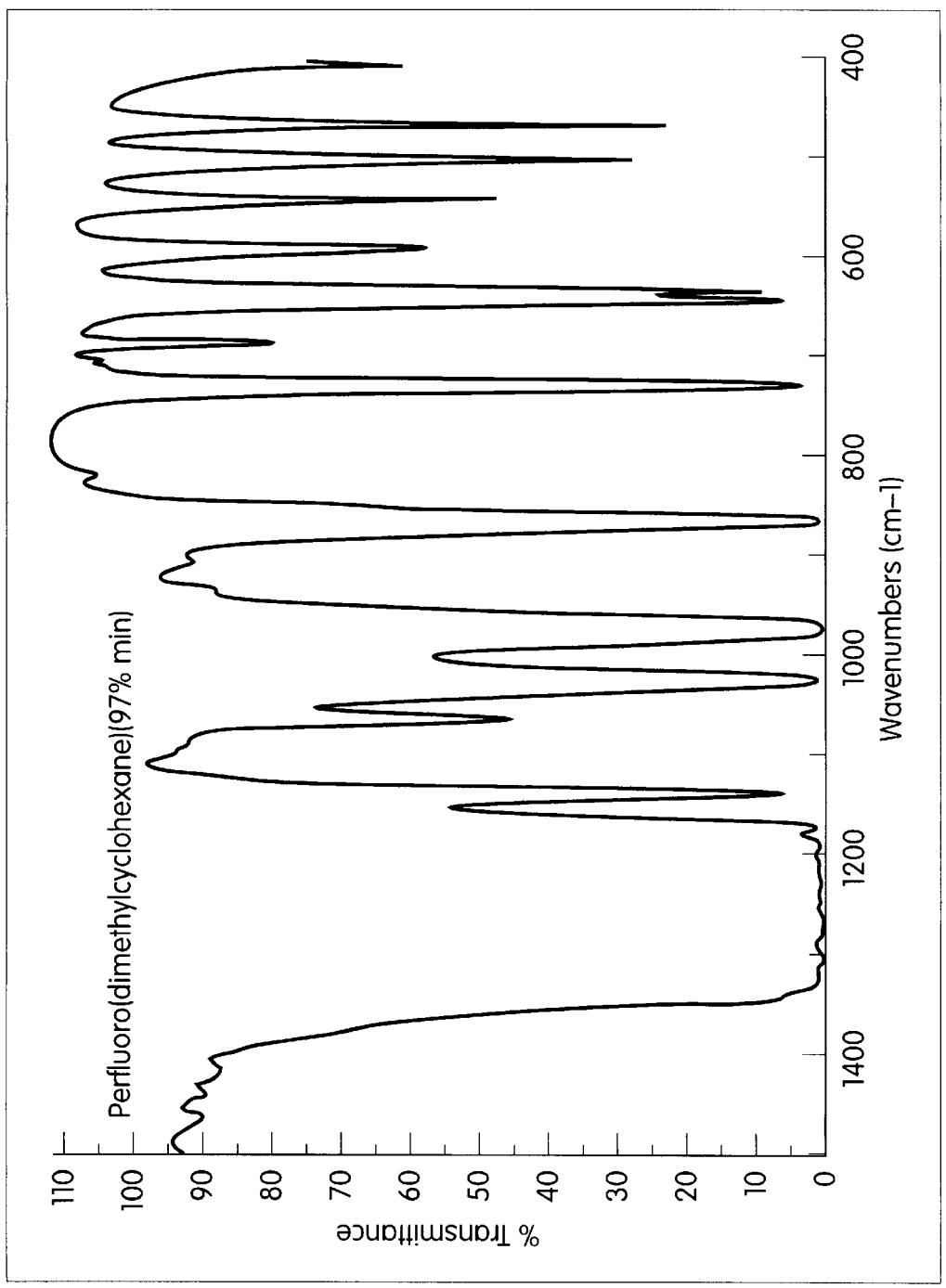
FIG. 5 is an enlargement of a section from the scan of FIG. 4 from approximately 1400 to approximately 500 wavenumbers ($cm^{-1}$), showing more detail.

FIG. 5 is an enlargement of a section from the scan of FIG. 4 from approximately 1400 to approximately 500 wavenumbers ($cm^{-1}$), showing in more detail the transmittance in that area.

In FIGS. 4 and 5, the transmittance scale is relative, accounting for the maximum value of 110%, i.e., in excess of 100% transmittance.

PFT Taggants

In addition to the PFTs noted in U.S. Pat. No. 4,256,038 discussed above, it has been discovered that the following PFT compositions are also particularly useful as taggants: perfluoro-methylcyclopentane (PMCP); perfluoro-1,2-dimethylcyclohexane (o-PDCH'); perfluoro-1,3-dimethylcyclohexane (m-pDCH'); perfluoro-1,4-dimethylcyclohexane (p-PDCH'); and perfluoro-trimethylcyclohexanes (PTCH).

Of the PFT taggants listed above, the following six are particularly preferred: PMCH, PMCP, o-PDCH', m-PDCH', p-PDCH', and PTCH. Any five of these six compositions may be combined, as desired, to form a specific "cocktail," i.e., a taggant that can be selectively detected and discriminated with respect to other taggants. Further, by varying the concentrations of taggants within the cocktail, a potentially greater number of tags may be generated, although specific authentication may require knowledge of the time of creation of the tag and the decay characteristics of each component of the tag. Likewise, the use of two or more taggants together in a fixed ratio may be used to determine the date of tagging, so long as the decay characteristics are relatively constant.

In order to prolong the usable life of a taggant, and control the release profile, it is preferred that a volatile taggant, such as a PFT, be encapsulated. Various encapsulation technologies are available, such as from Collaborative Technologies, Inc., East Setauket, N.Y. The encapsulated volatile taggant is then empirically evaluated for performance and manufacturability. Several approaches are possible to provide intelligent tags that release PFTs under certain preprogrammed conditions.

The test method employs a head-space gas chromatography technique using an electron capture detector (ECD). ECD is the detector of choice for these laboratory evaluations since it is highly sensitive to halogenated hydrocarbons, such as PFTS, and is a well known and documented technology. The optimal head-space sampling and instrumentation parameters for maximum sensitivity and selectivity for each PFT are determined. Ideally, encapsulated PFTs follow Fick's First Law of Diffusion which states that the flux of a core component across a membrane is independent of time, or follows zero order kinetics. Other mechanisms afford release profiles which are time dependent. See, Langer, Robert. Ed., Annals of The New York Academy of Sciences, on controlled release polymer technology. These effects are undesirable for PFT technology since the concentration of tracer release would otherwise vary with time. Initial PFT release rates are high and will "flood" the immediate environment with the tracer signal, which could lead to false positive detection. As time progresses, the signal intensity will decrease until the core is depleted. Time dependent core release mechanisms are promoted by encapsulation systems which change surface area over time (erodable microcapsules), or where the microcapsule surface is dominated by microchannels through which core substance(s) can escape.

Since prediction of the release profile of a core-encapsulation combination(s) is difficult or impossible, they must be determined experimentally. In order to identify an acceptable encapsulation technology, a range of off-the-shelf encapsulation technologies may be screened for their usefulness in developing PFT microcapsules with the desired properties. Generally, such technologies are scalable and can be used in the manufacture of commercial encapsulated PFT systems. Cyclodextrins, liposomes, and synthetic polymer systems can be used in the development of encapsulated PFTs. As a group, these technologies provide a menu of tracer devices which can be tailored to meet a specific need. Thus, it is apparent that the present invention does not necessarily limit the selection of the encapsulation process itself.

Cyclodextrin-PFT complexes can be formulated as a dispersion, true solution, or as solid crystalline powder. The cyclodextrin-PFT complexes can be made in water or mixed solvent systems and isolated as a free-flowing powder by spray drying or filtration from the mother liquor. The complex can be formulated in its mother liquor or used as an true solution or dispersion.

PFTs can also be encapsulated within liposomes. Liposomes are submicroscopic (<500 nm) capsules consisting of a double membrane comprised of phospholipids, a natural material commonly isolated from soy beans. They are non-toxic and generally recognized as safe (GRAS) by the FDA. They can be characterized as a hollow flexible sphere containing an aqueous internal compartment surrounded by an external aqueous compartment. Any material trapped inside the liposome is protected from the external environment. The lipid bilayer acts as a barrier and limits exchange of materials inside with materials outside the membrane. Furthermore, the lipid bilayers are hydrophobic and can "entrap" and retain similar types of substances such as PFTS. The ability to aerosolize liposomes is a potentially compelling advantage of PFT liposomes. The rate of release of tracer from a PFT liposome can be controlled by varying the fatty acid composition of the phospholipid acyl groups, or by providing elements which are embedded in the lipid bilayers, which specifically allow or control release of PFT from the liposomes. In practice, chemical modification of the phospholipid acyl groups is accomplished by either chemically modifying the naturally derived materials, or by selecting the appropriate synthetic phospholipid. The embedded elements in the liposome may be biologically or bioengineering derived proteins, polypeptides or other macromolecules to selectively provide pores in the liposome wall.

Over the past two decades, a wide range of encapsulation technologies has been developed using both natural and synthetic polymers. Synthetic polymers offer the best control over the performance of the PFT sustained release systems. These technologies range from the preparation of microcapsules with a core substance to thin film resins which contain the active material uniformly dispersed within a resin. The selection of polymer and processing method for a particular application is determined by the desired physical properties and release profile of the system. In order to prepare an encapsulated PFT which has the ideal release profile for PFTS, it is necessary to use polymers which possess the optimal crystallinity, glass transition temperature, permeability, and interactions with the PFTs. These characteristics generally have the greatest effect on the release rate of the tracer from encapsulated PFTs, although other characteristics may also influence the release rate. The encapsulation process parameters can be varied so they yield an encapsulated PFT which produces a constant and detectable signal over a suitable period of time before the system has expended its core substance. For example, the release profile of a particular encapsulated PFT can be modified by changing parameters such as polymer molecular weight, concentration, processing time, curing conditions, use of plasticizers, etc. Furthermore, the same polymer-PFT combination can be used to fabricate each of the encapsulation systems by varying the encapsulation process. In like manner, taggants other than PFTs, such as PFT derivatives and analogues may be encapsulated.

In order to evaluate encapsulated PFTs, various samples may be ranked according to their performance characteristics and ease of process scale-up. Ideally, systems will be identified as those which exhibit prolonged release of the tracer from the encapsulated PFT, and having a method of preparation which is amenable to scale-up.

The present inventors have developed the use of the perfluorocarbon tracer family of compounds for the tagging and detection of drugs, chemical compounds and currency, and subsequently tracking of the movement and location of vehicles and boats, or individuals involved in illegal activities or transport of contraband. Generally, the PFT tag may be delivered in a sealed container, to avoid contamination of law enforcement personnel, and applied to the "subject" surface (tagged object) by field agents. The "tagged" subject is thus able to emit a detectable signal for specified periods, such as between one week to one month, allowing agents to monitor the movement, identify the location, and to link individuals, locations and vehicles and vessels to specific criminal activities.

Although a gas chromatograph can detect PFTs in parts per billion, this technology is also subject to instability if placed in contact with a "burst" of PFT vapors. Therefore, an optical or spectral characterization method may provide increased dynamic range accommodation for bursts and low levels of taggant. A tunable laser, for example, may be used to scan a range of wavelengths to detect a taggant signature. Likewise, a UV laser may be used with a multichannel or wavelength scanning sensor to detect a taggant signature. These systems may be made portable while retaining their sensitivity and selectivity. Optical sensor devices can thus detect the existence of both an emitting tag (based on the volatile Perfluorocarbon Tracer Technology) and non-emitting tags.

This PFT tag technology and its relatively high vapor pressure provides the unique ability to permeate closed doors and windows, containers and luggage, and the taggant itself is immune to electronic interference and other problems inherent with electronic tagging technologies. Once a local environment reaches steady state, the actively emitting tagged item will provide vapor traces that are detectable in the vicinity of the item (even temporarily following removal of the tagged item). The encapsulation of the taggant extends the detectable life of the PFT tag materials and provides a unique tool for law enforcement in numerous applications including non-invasive inspection of locations and cargo under surveillance. The ability to mix several compositions of PFTs and then selectively detect such mixed compositions allows several intelligence scenarios to be conducted concurrently without cross operational interference or contamination (an important evidentiary consideration in law enforcement operations).

While continuous vapor emission is often desired, encapsulation technologies are known which selectively release composition in response to environmental conditions, such as temperature, pressure, touch, humidity, pH, light or specific illumination. These may be considered intelligent encapsulation technologies, especially where the release trigger corresponds closely with an event of interest. For example, the release of the tracer may be intelligently initiated either by the presence of the contraband itself, or when an item has been tampered with. A field portable laser/optical device is capable of detecting small traces of PFT vapors, without the inherent limitations associated with existing gas chromatographs (saturation), and is thus a preferred embodiment of the present invention.

The PFT tags have maintainable lives of between about one-week and one-month, or longer, and may provide highly reproducible tracer release profiles from batch-to-batch. The invention also provides custom designed tagging (tags and printers) and detection systems based on the Perfluorocarbon family of compounds and amenable to manufacturing processes which produce a high yield of microcapsules, show highly reproducible tracer release profile, are free of agglomeration, and possess a high efficiency of encapsulation of PFT. Where the release profile is too short, the taggant has a short half-life and must be provided fresh; further, after the taggant has been exhausted, the system will no longer reliably operate. On the other hand, where the release profile is too long, the amount of vapor release will be low, and a greater amount of taggant must be applied to achieve the same environmental concentrations. Further, the possibility of stray taggant in the environment will increase.

Laser Optical Detection System

It is preferred to use a laser-based optical detection system, which is capable of sensing taggant vapors remotely and stably in the field at parts per billion. The system preferably employs an excite and probe approach, directing low-energy pulses of laser light towards the object or area to be scanned for significant taggant vapor concentration, and measuring the level of light absorbed, reflected or fluoresced falling within characteristic wavelength regions which uniquely identify the presence of taggants. An all-solid state laser source amenable to diode-laser pumping are preferably employed, allowing the detection system to be compact, rugged, self-contained and portable. However, tunable dye lasers, excimer lasers, flash lamps and flash lamp excited lasers and other illumination sources may be employed as expedient.

The detection device identifies and measures spectral characteristic signatures from taggant vapor. Several types of PFTs have previously been shown to emit a characteristic fluorescence spectrum during and immediately following excitation with ultraviolet light. Thus, UV fluorescence characteristics are believed to be present in the PFT molecules. The use of modified or derivatized PFTs and PFT analogues may provide additional significant opportunities for reliable, specific and sensitive UV laser fluorescence detection of taggant. In providing a UV fluorescence system, an appropriate excitation wavelength is selected, such as 236 nm, based on availability of excitation source and production of an optimum laser induced signal from the taggants of interest. The sensor, which is generally integrated within a single housing with the excitation source, is coupled with appropriate fluorescence collection optics as well as detection and signal-processing electronics to allow sensitive extraction of the characteristic laser-induced fluorescence signature from ambient background radiation. The preferred laser is all solid state, and, if used at short range, may be based on frequency multiplying technologies (such as frequency doubling, tripling and quadrupling crystals).

The excitation source system may, for example, will generate wavelengths in the ultraviolet range, roughly between 180–300 nanometers (nm). Several promising candidate laser host materials exist that can be made to generate light in this spectral region through the use of frequency-quadrupling techniques, including Neodymium-doped YLF and Neodymium-doped YVO (vanadate). YLF and YVO are particularly attractive because they can be efficiently pumped by commercially available diode-laser-arrays, eliminating the bulk, external cooling water and three-phase power requirements of more typical arc-lamp or flashlamp-based laser power supplies. In the YLF or YVO systems, an IR laser signal from the YLF/YVO crystal is intracavity frequency-doubled using a KTP or LBO crystal, then extracavity doubled using either LBO or BBO, resulting in a frequency-quadrupled signal in the desired UV spectral region. Once the object or area under examination for PFT vapor has been illuminated with the appropriate excitation wavelength, a portion of any induced fluorescence radiation will be captured by an optical system, optically filtered to eliminate unwanted wavelengths, then imaged onto a UV-sensitive photodiode. Generally, measurements of a number of wavelengths are desired so that the selectivity of the system is maintained. Finally, electronic signal processing techniques is applied to the measured photocurrent, ensuring a high enough signal-to-noise ratio to allow parts-per-billion concentrations of PFTs to be reliably detected. Of course, other configurations of spectral characteristic detection systems are possible and may be employed.

Tagging, Detecting and Tracing of Currency, Packages and Cargo

PFT tracers are safe, non-reactive, environmentally benign and volatile gaseous compounds. The ambient background levels of the five routinely used PFTs are in the range of parts per $10^{15}$ of air. The present inventors hereof have successfully demonstrated a method of detecting the location of a bag containing 9 previously tagged bills. This demonstration employed gas chromatography as the detection method, and conclusively established PFTs as a useful tool for tracing currency and other objects. The addition of controlled release technologies and spectral characteristic detection of taggant greatly improves the utility of PFTs as practical taggants.

The application of the Perfluorocarbon Tracer (PFT) technology in the tagging, detecting and tracing of money, packages and cargo entails the tagging of currency and packages (which might be used in, or be part of an illicit drug transaction) with a PFT taggant for the purposes of subsequent tracing and identification. The innovation of utilizing Perfluorocarbon Tracer (PFT) technology to provide a method for noninvasive detection of detecting currency, packaging and wrappers used in illicit drug trade rests with its most basic technological improvement over existing drug detection techniques. Sampling the environment for trace levels of drugs involves collecting samples that may contain hundreds and perhaps thousands of different compounds. By using a PFT and a spectral characteristic detection system, it is necessary only to identify a single compound group.

The application of PFTs as a drug detection methodology involves detection by crime fighting agents and/or customs or treasury field inspectors, and the application of the taggant material through covert agents or ongoing programs. Timely examination of containers, cargo and vehicles for contraband without the need for physical disassembly is a key component in the war against drugs. This non-intrusive inspection poses great technical challenges that stem from basic as well as operational issues. PFTs and other taggants according to the present invention offer capabilities which are essential to having effective detection devices. These are: high penetrability, high sensitivity, high specificity, high-speed, non-intrusiveness and possibilities for automatic decision-making. The present invention thus allows agents to determine the presence or existence of pre-tagged money (paper currency) in packages under several different scenarios:

a) Tagging a selected shipment of money that may become involved in a drug transaction so that the currency can be detected without visual or intrusive inspection;

b) Tagging all or significant parts of the Federal currency to prevent the export of large quantities of cash which are often associated with major drug transactions; and c) Tagging parcels and/or packaging; i.e., containers of illicit drug related materials (e.g., currency, chemicals, manufacturing equipment and drugs themselves) in order to discretely trace their movements.

This application of PFTs will enable law enforcement agents to detect PFT vapor emissions in luggage containing currency used in drug transactions, as well as vehicles, containers and vessels in which drugs are being transported in a non-obtrusive manner.

It is important, for trace contraband detection, that residues are present on the exterior surfaces of contraband. It has been confirmed, in the course of many field and laboratory studies, that detectable residues are indeed present in virtually all cases of contraband concealment in luggage. Hence, the primary task is to seek out and detect contraband residues in luggage or cargo surfaces, which in turn infers that the contaminated luggage contains bulk contraband.

The use of PFTs in this context would likely provide agents the ability to "identify" transport vehicles even if there is no contraband cargo in the box, due to the residual emissions of PFTs. Previously tagged cargo will build-up a steady state concentration of PFTs; those vapors can be reliably detected at the vented locations on transportation vehicles, and from luggage and/or other shipping containers, even if the contraband cargo has been removed.

Previous research has proven that the use of microencapsulation of PFTs or other taggants can be useful for slow release in a tagged vehicle, container or package. Microcapsules with absorbed taggant can be adhered to cargo and will remain relatively inconspicuous. For example, previous research has shown that Styrofoam boxes, suitcases, attaches and heat sealed plastic bags are all poor barriers of PFTs due to the relative lack of air tightness. Even aluminum luggage with rubber gaskets does not prevent the detection of a vapor taggant. Field experiments have verified theoretical models of barrier enclosed explosives. The result indicates the ability for real-time detection of taggants using a taggant detection with a parts-per-trillion level of detection and a sampling system having a dilution factor of 1000. Another conclusion of the model is that the taggant concentration obtained in a moderately sized room fifteen minutes following the introduction of a severe barrier containing a taggant source of one nanoliter/minute emission rate (placed in the room one hour earlier) is sufficient to allow detection by a concentration detection scheme. A moderate barrier, such as a suitcase or box would allow real-time continuous detection of luggage moving on conveyor belt. With detectors that have a response time of approximately one second, or less, this application is fully practical.

Research originally conducted in the 1980s under sponsorship of the Bureau of Alcohol and Firearms of the U.S. Department of Treasury proved that PFTs were able to be micro-encapsulated for the purpose of tagging of blasting caps. This study concluded that vapor tagging of explosives for pre-detonation detection could be accomplished with the use of micro-encapsulated PFT taggants. Taggant-containing microcapsules were found to be able to be blended into both the bulk explosives as well as in the labels and closures. Once incorporated into or on bulk substances, vapor taggants permeate the microcapsule membrane and provide a detectable and uniform source of taggant.

In this study, taggant-containing microcapsules, manufactured by 3M, were examined. The capsule membrane material was a urea-formaldehyde polymer. The microcapsules were packed in tubing and then purged with $N_2$ to remove the released taggant for subsequent chromatographic analysis. Over a six month period, emission rates were found to be relatively constant.

Tagging and Detecting Processed or Final Product Drugs

The application of PFT technology in the tagging and detecting of processed or final product drugs can entail the tagging of crops by aerial spraying of fields or mixing finished or processed drugs with a taggant.

One method for the application of PFTs to illicit drugs is through "crop dusting" of drug precursors with PFTs, such as mixed within insecticides. This method has a particularly good likelihood of success given the fact that:

(1) current airborne drug eradication techniques which include crop spraying/dusting are being phased out due to adverse environmental and economic impact on legal crop production; and (2) the prior experience with impregnating explosive blasting cap which demonstrated the ability to detect emissions from caps which have been previously "tagged" with micro-encapsulated PFTs.

Detection can take place by drug agents and/or customs field inspectors, and the taggant can be applied through covert agents or spraying crops in a manner similar to the crop eradication program which is currently in its final stages.

The ability to impregnate an object or substrate (in this case, drug crops, packaged drugs, etc.) with PFTs and then being able to detect clandestine shipments at airport baggage handling areas provides a unique and unexpected "weapon" in the war on drugs.

Additionally, detection of drug use in the body and body fluids is also possible. Drug detection instrumentation can deliver immediate or accurate results for the presence, amount and history of tagged drugs in the body, for example by breath detection upon exhaling. Thus, PFTs may have medical applications, especially considering their low toxicity and high sensitivity and rapid detection.

In short, the known PFT technology may be applied to detecting the presence of tagged drug products during storage or shipment by truck, boat or airplane (i.e., pre-tagged drug cargo would emit detectable levels of PFTs from cargo holds or vents). This would allow agents to conduct a preliminary search of a suspected vehicle or vessel by spectral characteristic detection for localized sources of PFT emissions.

Furthermore, the use of PFTs would likely provide agents the ability to "identify" transport vehicles even if there is no contraband cargo on-board, due to the residual emissions of PFT.

Based on previous research demonstrated on a 727 aircraft, where a single stick of explosive, tagged with PFTs, was detected through the rear outflow valve of the aircraft, it is known that tagged objects, including drugs, will build up a steady state concentration of PFTs and that vapors will be reliably detected at the vented locations on transportation vehicles.

Wide Area Surveillance of Illicit Botanical Laboratories and Other Processing Facilities The application of PFT technology in the tagging and detecting and wide area surveillance of botanical laboratories and other processing entails the tagging of chemicals used in the processing of crops associated with the illicit drug trade. Detection of these laboratories may, for example, take place by airborne or land-based agents searching for these facilities in jungle and other sub-tropical, or highly congested urban areas. The taggant could be applied under law, by the manufacturers of the most commonly used additives, chemicals and solvents used in the drug trade. Thus, the present invention makes it possible to detect tagged chemicals and laboratories utilizing them, both on the ground and through airborne (over flights of the suspected areas) and mobile sensors.

PFT technology has been shown to provide accurate atmospheric tracing and air flow measurements across wide-areas of geography. Therefore, agricultural tagging and detection is believed possible over these widely varying environmental conditions.

Additionally, an air dispersion test using PFTs was conducted in 1993 to identify the source of the haze over the Grand Canyon. Through the detection of the various PFTs released from known sources of the pollution, the actual source was pinpointed at a power plant located over 100 miles down stream. In other experiments, tracer releases were made over a three month period with sampling out to distances of 3000 km at concentrations down to $0.5 \times 10^{-15}$ L/L of air.

The present invention has its scientific basis in work previously conducted during a Cross North America Tracer Experiment. During this experiment, three PFTs were released at an industrial park, both in "flatlands" devoid of vegetation and at sites where trees were 100 meters in height, At the release locations, the tracers were evaporated into a heated air stream through a stove pipe ending two meters above the roof of a one story building.

Aircraft were then used, each with the capability to automatically collect twenty air samples which were later sent to a laboratory for PFT analysis. In addition to the collected samples, the aircraft was also equipped with a two-trap sampler, PFT analyzer for real time tracer plume detection. The plane flew at a speed of 250 Km/hour at 500–1500 feet.

Sampling usually occurred soon after the release of the PFTs, but for several night time releases during conditions of strong surface based inversions with light winds, sampling was delayed until the next day when the plume mixed high enough for aircraft sampling. The aircraft frequently flew perpendicular to the plume, back and forth along a line at the same or different altitudes. Based on study findings, PFT concentrations in the plume sampled from aircraft were typically two orders of magnitude greater than ground level samples.

The fixed ground and airborne sampling data, when coupled with known weather and atmospheric data, can provide the total picture leading to an accurate back track to the PFT emissions source.

In 1988, an experiment was conducted on the ground to detect a leak in a tagged natural gas line for a utility. Utilizing passive Capillary Absorption (sampling) Tubes mounted on telephone poles (POLE CATS), the underground leak was detected within one-half block by the passive tubes. When utilizing a continuously operating Perfluorocarbon Sniffer (COPS), the leak was pin-pointed to within a few feet. This specific experiment demonstrates the capability for urban and high density tagged chemical detection using conventional PFT sniffing equipment.

There has thus been shown and described a novel method of tagging and detecting objects, including illicit drugs, crops, chemical compounds and currency with perfluorocarbon tracers (PFTs) and related compounds which fulfills all the objects and advantages sought therefor. Many changes, modifications, variations and other uses and applications of the subject invention will, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. A method of detecting the presence or proximity of an object, comprising the steps of:

(a) applying a volatile tracer to the object as a taggant; and (b) subsequently detecting the presence of said taggant by the absorption, transmittance, reflectance, photon emission or fluorescence spectral characteristics of the taggant, to determine the presence or proximity of the object.

2. The method defined in claim 1, further comprising the step of illuminating a space to be sensed for the presence of taggant, wherein the illumination is cooperative with the detection, further comprising the steps of synchronizing the illumination with the detection and processing a detected signal based on said synchronization for increased detection sensitivity.

3. The method defined in claim 1, wherein said applying step comprises the step of subjecting the object to a PFT vapor.

4. The method defined in claim 1, wherein said applying step comprises the steps of:

(a) encapsulating a taggant in a plurality of microcapsules; and (b) applying said microcapsules with said encapsulated taggant to the object.

5. The method defined in claim 1, wherein the object comprises illicit drugs, and the taggant comprises a Perfluorocarbon Tracer (PFT), applied to a container of illicit drug related material, such that said PFT is released from said container over a period of time as a vapor taggant.

6. The method defined in claim 1, wherein an illumination source is provided for detecting the absorption, transmittance, reflectance, photon emission or fluorescence spectral characteristics of the taggant, the illumination source being cooperative with the detector.

7. The method defined in claim 1, wherein the detecting step comprises detecting a fluorescent emission from a taggant excited by a pulsed illumination source, the detecting step further comprising the step of determining a background signal from the object when the illumination source is not pulsing and compensating detection for the background signal.

8. The method defined in claim 1, further comprising the step of illuminating a space to be sensed for the presence of taggant, wherein the illumination is cooperative with the detection, further comprising the steps of synchronizing the illumination with the detection and processing a detected signal based on said synchronization for increased detection sensitivity.

9. The method defined in claim 1, wherein the taggant exhibits UV fluorescent characteristics.

10. The method defined in claim 1, wherein the taggant is microencapsulated and selectively released in response to one or more stimuli selected from the group consisting of light, specific illumination, heat, pressure, touch, humidity, pH, and receptor binding.

11. The method defined in claim 1, wherein said applying step comprises the steps of:
 (a) dissolving a taggant composition in a liquid carrier; and
 (b) applying said liquid carrier with said dissolved composition to the object.

12. The method defined in claim 11, wherein said liquid carrier is an oil.

13. The method defined in clam 11, wherein said object is a document and said carrier is an oil.

14. The method defined in claim 11, wherein said carrier is a substantially clear liquid.

15. The method defined in claim 1, wherein the absorption, transmittance, reflectance, photon emission or fluorescence of the taggant is detected after laser illumination.

16. The method defined in claim 15, wherein the laser is an ultraviolet laser.

17. The method defined in claim 15, wherein the illuminator is a pulsed, high energy laser which provides stimulation at the wavelength at which the taggant is most sensitive and which produces absorption, transmittance, reflectance, photon emission or fluorescence at a wavelength to which the sensor is sensitive.

18. The method defined in claim 15, wherein the laser is an ultraviolet laser.

19. The method defined in claim 15, wherein the illuminator is a pulsed, high energy laser which provides stimulation at the wavelength at which the taggant is most sensitive and which produces absorption, transmittance, reflectance, photon emission or fluorescence at a wavelength to which the sensor is sensitive.

20. The method defined in claim 1, wherein the object comprises a drug.

21. The method defined in claim 20, wherein said applying step comprises the steps of:
 (b) dissolving a taggant in a liquid carrier; and
 (c) treating a precursor required in the manufacture of the drug with the liquid carrier with the dissolved taggant.

22. The method defined in claim 20, wherein the object comprises a drug outside legal channels of distribution.

23. The method defined in claim 22, wherein said treating step comprises the step of spraying crops which are used in the manufacture of drugs with a liquid carrier with the dissolved taggant.

24. The method defined in claim 22, wherein said treating step comprises the step of applying a taggant to a chemical composition which is used as a precursor in the manufacture of a drug.

25. The method defined in claim 1, further comprising the step of illuminating a space to be sensed for the presence of taggant.

26. The method defined in claim 25, wherein said light is in the ultraviolet, visible or infrared sections of the electromagnetic spectrum, or in a combination of two or all of those sections.

27. The method defined in claim 25, wherein the illumination is in the ultraviolet, visible or infrared sections of the electromagnetic spectrum, or in a combination of two or all of those sections.

28. The method defined in claim 25, wherein said step of illuminating comprises directing a laser toward the space.

29. The method defined in claim 28, wherein said laser is an ultraviolet laser.

30. The method defined in claim 28, wherein said laser is an ultraviolet laser.

31. The method defined in claim 1, wherein the absorption, transmittance, reflectance, photon emission or fluorescence spectral characteristics of the taggant are detected by a detector after illumination by an illuminator, the illuminator and the detector being spatially separated.

32. The method defined in claim 31 wherein the illuminator is located in a flying object.

33. The method defined in claim 31, wherein the detector is located in a flying object.

34. The method defined in claim 31 wherein the illuminator is located in a flying object.

35. The method defined in claim 31, wherein the detector is located in a flying object.

36. The method defined in claim 35, wherein the detector is either in geostationary orbit or low earth orbit.

37. The method defined in claim 35, wherein the absorption, transmittance, reflectance, photon emission or fluorescence is within at least one of the bands of atmospheric transmission in which a detector can receive electromagnetic signals from the ground.

38. The method defined in claim 37, wherein the band is the MWIR band at about 3.1 $\mu$m or the visible band above 0.4 $\mu$m.

39. The method defined in claim 31, wherein the illuminator is cooperative with the detector, the illuminator being triggered when the object of interest is within a field of view of the detector.

40. A method for detecting a volatile taggant having spectral characteristics within a sample space, comprising:
 (a) illuminating the sample space;
 (b) detecting a spectral characteristic of energy from the sample space;
 (c) comparing the spectral characteristic to a predetermined spectral characteristic pattern; and
 (d) outputting a signal relating to a result of said comparing.

41. The method according to claim 40, further comprising the steps of:
 (a) detecting an electron capture characteristic of a sample from the sample space;
 (b) comparing the electron capture characteristic to a predetermined electron capture characteristic pattern; and
 (c) outputting a signal relating to a result of said comparing.

* * * * *